PROCESS FOR THE METHYLATION OF PHENOLIC COMPOUNDS

BACKGROUND OF THE INVENTION

This invention is directed to a process for methylating phenolic compounds having at least one replaceable hydrogen on the aromatic ring. More particularly, this invention is directed to a process for methylating phenol with methane.

Recently, several different methods have been proposed for methylating phenols. Methylated phenols include: cresols, xylenols and higher methylated phenols like di- and tri-methylphenol.

One such method is taught in an article entitled, "Alkylation of Phenol with Methane Over Solid Acids and Bases," by Tadao Nishizaki and Kozo Tanabe in Chemistry Letters, Pages 149-150, No. 2, February 1973, which is published by the Chemical Society of Japan. This method involves the alkylation of phenol with methane over silica-alumina; or alumina catalyst. The alkylation is conducted at a temperature in the range of 400°-500° C. and at atmospheric pressure. This article also teaches that catalysts such as silica-titania, magnesia-alumina, and magnesium oxide are catalytically inactive in the alkylation of phenol with methane.

Another methylation process is taught in U.S. Pat. No. 3,718,704 (Chapman, et al.). This process for methylating an organic compound, e.g., an aromatic compound with an hydroxy group, includes contacting the methylatable compound with carbon oxide containing reactant gas in the presence of an oxide of Group IB, IIB, and/or VIB metal containing catalyst at a temperature between 400° F. (204° C.) and about 1200° F. (649° C.). This patent also teaches that no appreciable methylated products were obtained when the conditions of the patent were employed, but catalysts were used that were different from those previously stated, for example, various supported catalysts like Group VIII metal oxides.

U.S. Pat. No. 3,822,271 (Lapporte) teaches another methylation process. This process involves methylating alkyl substituted benzenes, aniline, pyridine, and alkyl substituted aniline and pyridine compounds by a mixture of carbon dioxide and hydrogen in the presence of a Fischer Tropsch catalyst like hydrogen reduced oxides or borides of cobalt and/or nickel. The methylation is conducted at a temperature in the range of 150°-450° C. and at a pressure of 1.7-70 atmospheres.

Other methylation processes known in the art prepare ortho-methylphenols by reacting a phenol at a temperature in the range of 300° C.-450° C. with methanol in the presence of ferrite catalysts which contain a divalent metal selected from zinc, magnesium, cobalt, nickel, chromium or cadmium or a catlyst which is a sintered methane-containing of ferric oxide and at least one of the aforementioned divalent metal oxides and a small amount of manganese oxide.

The process for methylating phenols described herein is believed patentable over the known prior art because the prior art does not teach or suggest to one skilled in the art, and actually teaches away from, a method for methylating phenolic compounds with methane in the presence of specific metallic catatlysts.

SUMMARY OF THE INVENTION

Somewhat surprisingly, I have found that contrary to the teachings of the prior art, phenolic compounds can be methylated with methane in the presence of metallic catalysts selected from nickel or cobalt or mixtures compound thereof. The process of methylating the phenolic compound involves reacting the phenolic compound with a methane-containing gas in the presence of a metallic catalyst selected from nickel, cobalt or mixtures thereof at a temperature in the range of about 300° C. to around 475° C.

The term "phenolic compounds" includes, generally, a phenol with at least one replaceable hydrogen on the aromatic ring. Examples of these compounds include: phenol (monohydroxybenzene); alkylated phenols, for example, cresol and ethyl phenols; xylenols, and resorcinol, hydroquinone, catechol and their methylated and ethylated derivatives. The term "methane-containing gas" includes a gas which contains a substantial amount of methane, around at least fifty percent (50%) by weight, and may contain lesser amounts of inert gases such as nitrogen. Generally, the molar ratio of phenolic compounds to methane is in the range of about 0.5:1 to around 5:1. Although molar ratios outside this range could be used, such use would be uneconomical.

The methylation process of this invention is usually conducted at atmospheric pressure, but it may be conducted at super-atmospheric or sub-atomspheric pressures with a concomitant adjustment in the temperatures. The metallic catalyst is generally used in an amount to provide good contact times for the reactant. The metallic catalyst may be used alone or on an inert support such as kieselguhr, magnesia, silica, thoria, zirconia, titania, alumina, charcoal, and the like. In addition to the metallic catalyst being nickel or cobalt, the catalyst may consist of a mixture of nickel and cobalt in any proportions and with or without an inert support. The metallic catalyst may also contain a minor amount of the oxide of the nickel or cobalt metal present in the metallic catalysts. The metallic catalysts used in the methylation process of this invention may be made in any manner known to those skilled in the art.

The process of this invention yields ortho-, meta-, and para-cresol with lesser amounts of higher methylated phenols when the starting phenolic compound is phenol. When the starting phenolic compound is an alkylated phenol with at least one replaceable hydrogen atom on the aromatic ring, the process of this invention yields higher methylated phenols. The yields of methylated phenolic compounds obtained with the use of a metallic catalyst selected from nickel, cobalt or mixtures thereof are generally better than yields obtained with the use of alumina or silica-alumina catalysts.

DETAILED DESCRIPTION OF THE INVENTION

The methylation process of this invention is conducted under certain general conditions of temperature, equipment, manner of operation and contact time, but there are optimum conditions at which this process can be conducted depending upon the particular metallic catalyst used. The optimum conditions for a particular metallic catalyst may vary from other optimum conditions for other particular metallic catalysts; but all of the optimum conditions will still be within the generally specified conditions.

Generally, the methylation process of this invention can be performed in any reactor known by those skilled in the art to be used for vapor phase catalytic reactions. Examples of these reactors are: fixed bed reactors, jiggling bed reactors, moving bed reactors or fluidized bed United States Patent [19]
Leston

[11] 4,158,101
[45] Jun. 12, 1979

[54] PROCESS FOR THE METHYLATION OF PHENOLIC COMPOUNDS

[75] Inventor: Gerd Leston, Pittsburgh, Pa.

[73] Assignee: Koppers Company, Inc., Pittsburgh, Pa.

[21] Appl. No.: 787,891

[22] Filed: Apr. 15, 1977

[51] Int. Cl.² ........................ C07C 37/12; C07C 39/06
[52] U.S. Cl. .................................... 568/804; 585/467; 585/470
[58] Field of Search ........... 260/621 R, 290 R, 671 R, 260/671 C, 626 C, 626 R, 671 M, 290 R; 568/804, 790

[56] References Cited
U.S. PATENT DOCUMENTS

| 3,718,704 | 2/1973 | Chapman et al. | 260/671 M |
| 3,822,271 | 7/1974 | Lapporte | 260/290 R |
| 3,923,907 | 12/1975 | Kotanigawa et al. | 260/621 R |

OTHER PUBLICATIONS

Nishizaki et al., "Chemical Society of Japan", Chem. Letter, pp. 149–150 (1973).

Primary Examiner—Werren B. Lone
Attorney, Agent, or Firm—J. Timothy Keane; Herbert J. Zeh, Jr.; Oscar B. Brumback

[57] ABSTRACT

Phenolic compounds are methylated with methane in the presence of a metallic catalyst selected from nickel or cobalt or mixtures thereof at a temperature in the range of about 300° C. to around 475° C.

9 Claims, No Drawings fixed bed catalyst reactor is maintained preferably within the range of about 380 to around 430° C.

An example of another metallic catalyst that can be used in the process of this invention is a reduced nickel oxide on a silica support. The nickel oxide on silica catalyst can be obtained by the designation T-1502A from Girdler Catalyst Department of Chemetron Chemicals Division, Chemetron Corporation.

After a period of time of catalyzing the reaction, the metallic catalyst may become deactivated because of a coating of carbon on the catalyst. The carbon coating has a tendency to deactivate the catalyst. The deactivated metallic catalyst may be reactivated in the fixed bed catalyst reactor after the reactor has shut down or in a separate stage of the fixed bed catalyst reactor or in a separate reactor. The separate reactor may be a fixed bed, moving bed or fluidized bed regenerator. The deactivated metallic catalyst is subjected to hot air and/or steam at a temperature of around 450° C. to burn the carbon coating from the deactivated catalyst. After the carbon coating is purged, the metallic catalyst then may have to be reactivated with hydrogen before it can again catalyze the methylation reaction.

In order to more fully illustrate the methylation process of this invention, reference is made to Table I. This table contains data for several experiments wherein phenol and methane were reacted in the presence of either Harshaw nickel catalyst NI-0104, reduced Girdler nickel catalyst G-65, reduced Houndry nickel catalyst Houdralite 715X2-4, or reduced Harshaw cobalt catalyst CO-0101. Table I also contains several experiments wherein phenol and methanol were reacted over a fixed bed catalyst of either alumina or silica-alumina. The data on these runs are included in Table I in order to show the unexpected results that the use of a metallic catalyst selected from the group of nickel, cobalt or mixtures thereof yield increased amounts of methylated phenols over the amount of methylated phenols obtained from an alumina-silica catalyst or an alumina catalyst.

TABLE I

METHYLATION OF PHENOL USING METHANE (1/1 mole ratio-single pass)

| Expt. No. | Catalyst | Max. Temp. °C. | GC Analyses, Area Percent | | | | | | |
|---|---|---|---|---|---|---|---|---|---|
| | | | Phenol min.-max. | o-Cresol min.-max. | m,p-Cresols min.-max. | $Me_2$, $Me_3$ and $Me_4$ Phenols min.-max. | Benzene min.-max. | Toluene min.-max. | Phenyl Ether min.-max. |
| 1 | Nickel, Ni-0104-Harshaw | 318 | 98.74–99.99 | 0.02–1.26 | | | | | |
| 2 | Nickel, Ni-0104-Harshaw | 375 | 95.66–99.68 | 0.25–2.04 | | | 0.07–2.10 | 0–0.20 | |
| 3 | Nickel, Ni-0104-Harshaw | 383 | 81.40–89.15 | 2.56–5.65 | | | 6.20–11.78 | 0.38–0.81 | |
| 4 | Reduced[2] Nickel Hydrogenation, G-65-Girdler | 380 | 98.51–99.20 | 0.17–0.47 | | | 0.63–1.02 | | |
| 5 | Reduced[2] Nickel Hydrogenation, G-65-Girdler | 440[1] | 89.32–89.70 | 5.88–6.12 | 0.07–0.11 | 0.20–0.21 | 3.10–3.38 | 0.72–1.11 | |
| 6 | Reduced[2] Nickel Oxide on Silica, T-1502A-Girdler | 386 | 99.49–99.84 | 0–0.14 | | | 0.16–0.37 | | |
| 7 | Reduced[2] Nickel Oxide on Silica, T-1502A-Girdler | 425[1] | 95.39–95.86 | 2.09–2.44 | 0–0.02 | 0–0.26 | 1.68–1.78 | 0.13–0.19 | |
| 8 | Reduced[2] Nickel, Houdralite 715X2-4-Houdry | 378 | 95.97–97.12 | 1.74–2.05 | | | 1.10–1.90 | 0.04–0.08 | |
| 9 | Reduced[2] Nickel, Houdralite 715X2-4-Houdry | 444 | 86.54–89.91 | 5.16–7.48 | 0.51–0.62 | 0.60–0.97 | 2.76–2.85 | 0.77–1.30 | 0.17–0.23 |
| 10[4] | Reduced[2] Cobalt, CO-0101-Harshaw | 380 | 93.00–97.23 | 0.76–2.63 | | 0–0.56 | 1.94–2.95 | 0.07–0.73 | 0–0.07 |
| 11[4] | Reduced[2] Cobalt, | 423 | 43.59–74.59 | 4.95–7.41 | 0.68–0.70 | 3.13–20.09[3] | 6.41–10.60 | 5.01–10.57 | 1.47–5.38 |
| 12 | Activated Gamma Alumina, T-374-Girdler | 380 | 97.35–98.98 | 0.81–1.85 | 0.02–0.12 | 0.18–0.59 | 0.01–0.03 | | 0.12–0.77 |
| 13 | Activated Gamma Alumina, T-374-Girdler | 413 | 89.57–97.73 | 1.12–2.46 | 0.05–3.79 | 0.18–2.09 | 0.06–0.30 | 0–0.07 | 0–1.62 |
| 14 | Houdry 100S (Alumina) | 373 | 97.09 14 98.74 | 1.26–2.91 | | | | | |
| 15 | Houdry 100S (Alumina) | 409 | 96.68–99.78 | 0.11–1.06 | 0.11–1.01 | 0–0.89 | 0–0.04 | | 0–0.32 |

[1]High exotherm caused catalyst fusion at this temperature and plugging resulted.
[2]$H_2$ reduced for 3–5 hours prior to use.
[3]2,3,6-Trimethylphenol of 3.03–18.85% and tetramethylphenol of 0.10–1.24%.
[4]Other components included Cyclohexanol and Anisole.

According to the provisions of the Patent Statutes, the principle, preferred construction and mode of operation of the invention have been explained and what is considered to represent its best embodiment has been illustrated and described. However, it should be understood that within the scope of the appended claims, the inventions may be practiced otherwise than as specifically illustrated and described.

I claim:

1. A process for methylating mononuclear phenolic compounds, comprising:
   (a) reacting a mononuclear phonolic compound selected from the group consisting of phenol, phenols substituted with one to four primary alkyls each of one to six carbon atoms, phenols substituted with one to four secondary alkyls each of one to six carbon atoms, resorcinol, hydroquinone, catechol, and the methylated and ethylated derivatives of one to three primary or secondary alkyl group substituted resorcinol, hydroquinone and catechol with a methane-containing gas in the presence of a metallic catalyst selected from the group consisting of nickel, cobalt, and mixtures thereof at a temperature in the range of about 300° C. to about 475° C. to produce methylated mononuclear phenolic compounds.

2. Process according to claim 1 wherein the mononuclear phenolic compound is phenol and the methane-containing gas is natural gas and the methylated mononuclear phenolic compounds are mainly ortho-cresol in a predominant amount and lesser amounts of meta- and para-cresol and di-, tri- and tetra-methylated phenols.

3. Process according to claim 1 wherein the mononuclear phenolic compound and methane-containing gas are reacted at atmospheric pressure.

4. Process according to claim 1 wherein the metallic catalyst selected from the group consisting of nickel, cobalt and mixtures thereof are supported on inert supports selected from the group consisting of kieselguhr, magnesia, silica, thoria, zirconia, titania, alumina, and charcoal.

5. Process according to claim 1 wherein the metallic catalyst is a nickel oxide deposited on gamma and alpha alumina and which is subjected to reduction by passing hydrogen over the catalyst for a period of about 3–5 hours and which is used to catalyze the reaction between mononuclear phenolic compounds and a methane-contanining gas at a temperature of about 300° C. to around 450° C.

6. Process according to claim 1 wherein the metallic catalyst is a cobalt oxide deposited on kieselguhr which is subjected to reduction by passing hydrogen over the catalyst for a period of about 3–5 hours and which is used to catalyze the reaction between the mononuclear phenolic compound and methane-containing gas at a temperature in the range of about 375° C. to around 430° C.

7. Process according to claim 1 wherein the metallic catalyst has 58 percent total nickel content on kieselguhr wherein the ratio of nickel oxide to nickel is 0.6/0.65 which is used to catalyze the reaction between the mononuclear phenolic compounds and methane-containing gas at a temperature in the range of about 300° C. to around 430° C.

8. Process according to claim 1 wherein the metallic catalyst is a nickel oxide deposited on a silica-alumina support which is subjected to reduction by passing hydrogen over the catalyst for a period of about 3 to around 5 hours.

9. Process according to claim 1 wherein the catalyst is in a fixed bed reactor.

* * * * *